United States Patent
Zubarev et al.

(10) Patent No.: US 9,138,418 B2
(45) Date of Patent: Sep. 22, 2015

(54) THERAPEUTIC COMPOSITIONS AND METHODS FOR DELIVERY OF ACTIVE AGENTS CLEAVABLY LINKED TO NANOPARTICLES

(75) Inventors: Eugene Zubarev, Houston, TX (US); Jacob Gibson, Houston, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 13/514,847

(22) PCT Filed: Dec. 9, 2010

(86) PCT No.: PCT/US2010/059704
§ 371 (c)(1),
(2), (4) Date: Sep. 19, 2012

(87) PCT Pub. No.: WO2011/072133
PCT Pub. Date: Jun. 16, 2011

(65) Prior Publication Data
US 2013/0004523 A1 Jan. 3, 2013

Related U.S. Application Data

(60) Provisional application No. 61/285,050, filed on Dec. 9, 2009.

(51) Int. Cl.
| | |
|---|---|
| *A61K 31/337* | (2006.01) |
| *B82Y 5/00* | (2011.01) |
| *C07F 1/12* | (2006.01) |
| *A61K 9/51* | (2006.01) |
| *A61K 47/48* | (2006.01) |

(52) U.S. Cl.
CPC ......... *A61K 9/5115* (2013.01); *A61K 47/48953* (2013.01); *B82Y 5/00* (2013.01)

(58) Field of Classification Search
None
See application file for complete search history.

(56) References Cited

U.S. PATENT DOCUMENTS

| | | |
|---|---|---|
| 6,265,540 B1 | 7/2001 | Isaacs et al. |
| 6,410,514 B1 | 6/2002 | Isaacs et al. |
| 6,504,014 B1 | 1/2003 | Isaacs et al. |
| 6,545,131 B1 | 4/2003 | Isaacs et al. |
| 7,053,042 B1 | 5/2006 | Denmeade et al. |
| 7,468,354 B2 | 12/2008 | Isaacs et al. |
| 7,635,682 B2 | 12/2009 | Denmeade et al. |
| 7,767,648 B2 | 8/2010 | Isaacs et al. |
| 2006/0222595 A1 | 10/2006 | Mukherjee et al. |
| 2007/0160536 A1 | 7/2007 | Denmeade et al. |
| 2008/0247950 A1 | 10/2008 | Denmeade et al. |
| 2009/0163426 A1 | 6/2009 | Isaacs et al. |

OTHER PUBLICATIONS

Hwu et al (J American Chemical Society, 2009, 131:66-68; published online Dec. 10, 2008).*
Gibson et al (J American Chemical Society, 2007, 129:11653-11661).*
Paciotti et al (Drug Development Research, 2006, 67:47-54).*
Aryal et al (J Mater. Chem. 2009, 19:7879-7884, published online Sep. 18, 2009).*
Hwu et al (J Am. Chem. Soc., 2009, 131:66-68; published online Dec. 10, 2008).*
Rodrigues et al (Bioorganic & Medicinal Chemistry letters, 20003, 13:355-360).*
Leonelli et al (Helvetica Chimica Acta, 2005, 88:154-158).*
Chen et al (J Med Chem, 2005, 48:1098-1106).*
International Search Report and Written Opinion for PCT/US10/59704 (Issued on Feb. 8, 2011).
Hainfield, et al., "The use of gold nanoparticles to enhance radiotherapy in mice", Phys. Med. Biol. 49 (2004) N309-N315.
Paciotti et al., "Colloidal Gold Nanoparticles: A Novel Nanoparticle Platform for Developing Multifunctional Tumor-Targeted Drug Delivery Vectors", Drug Development Research, 2006, vol. 67, Issue 1, pp. 47-54.
Zakharian et al., "A fullerene-paclitaxel chemotherapeutic: synthesis, characterization, and study of biological activity in tissue culture." Journal of the American Chemical Society, 2005, vol. 127, Issue 36, pp. 12508-12509.
Tong et al., "Anticancer Polymeric Nanomedicines." Polymer Reviews, 2007, vol. 47, Issue 3, pp. 345-381.
Zubarev Research Group. Tumor Specific Delivery of Paclitaxel via pH Responsive Gold Nanoparticles. Nov. 11, 2010.
Gibson et al., "Paclitaxel-functionalized gold nanoparticles" Journal of the American Chemical Society, 2007, vol. 129, Issue 37, 11653-11661.

* cited by examiner

Primary Examiner — Laura B Goddard
(74) Attorney, Agent, or Firm — Winstead PC

(57) ABSTRACT

Various embodiments of the present invention pertain to therapeutic compositions that comprise: (1) an active agent (e.g., paclitaxel); and (2) a nanoparticle (e.g., gold nanoparticle). In such embodiments, the active agent is covalently linked to the nanoparticle through a cleavable linker (e.g., a linker containing a hydrazone species). Other embodiments of the present invention pertain to methods of treating a condition in a subject by administering the above-described therapeutic compositions to the subject.

12 Claims, 3 Drawing Sheets

THERAPEUTIC COMPOSITIONS AND METHODS FOR DELIVERY OF ACTIVE AGENTS CLEAVABLY LINKED TO NANOPARTICLES

CROSS REFERENCE TO RELATED APPLICATIONS

This application claims priority to U.S. Provisional Patent Application No. 61/285,050, filed on Dec. 9, 2009, the entirety of which is incorporated herein by reference.

STATEMENT REGARDING FEDERALLY SPONSORED RESEARCH

This invention was not funded by any federally sponsored research grants.

BACKGROUND OF THE INVENTION

Current methods for delivering active agents to desired sites in an organism suffer from various limitations. For instance, many active agents, such as anti-cancer drugs (e.g., paclitaxel), act in a non-specific manner against both diseased cells and normal cells. Such non-specificity can cause undesired side effects in a subject (e.g., nausea, hair loss, reduced immune response, etc.). The non-specificity of many active agents can also reduce their therapeutic efficacy.

To alleviate the above-mentioned problems, active agents have been linked to numerous carriers, such as nanoparticles. However, such methods also suffer from various limitations. For instance, many carriers may not be able to effectively deliver and/or release the active agents at desired sites. This problem can be further amplified by the lack of solubility of many active agents and/or carriers. Accordingly, there is currently a need to design more effective approaches for the delivery of active agents to desired sites for treating various diseases and conditions (including cancer).

BRIEF SUMMARY OF THE INVENTION

In some embodiments, the present disclosure pertains to therapeutic compositions that comprise an active agent and a nanoparticle, where the active agent is covalently linked to the nanoparticle through a cleavable linker. In some embodiments, the active agent is an anti-cancer drug, such as paclitaxel. In some embodiments, multiple active agents may be covalently linked to the nanoparticle through cleavable linkers. In some embodiments, the active agent is substantially inactive when it is covalently linked to the nanoparticle.

In some embodiments, the cleavable linker is a chemically cleavable linker, such as a linker that comprises a hydrazone species that can release the active agent(s) from the nanoparticle in an acidic environment (e.g., a tumor site).

In some embodiments, the nanoparticle is a gold nanoparticle (AuNP), such as a gold nanoparticle with a diameter of about 2 nm. In some embodiments, the nanoparticle is functionalized with one or more functional groups and/or polymers, such as polyethylene oxide (PEO). In some embodiments, the therapeutic composition may also comprise a targeting agent, such as an antibody, for directing the therapeutic composition to a desired site.

Additional embodiments of the present disclosure pertain to methods of treating a condition in a subject by administering the therapeutic compositions of the present disclosure to the subject. In some embodiments, the subject is a human being, and the condition to be treated is cancer. In such embodiments, the cleavable linker in the therapeutic composition may be cleaved at or near a tumor site in the subject to release the active agent at that site. In some embodiments, the active agent is substantially inactive when it is covalently linked to the nanoparticle. In such embodiments, the cleaving and subsequent release of the active agent results in its activation.

The methods and compositions of the present invention allow for more effective and specific approaches for treating many diseases with reduced side effects, streamlined treatment formulations, and improved patient outcomes.

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated in the appended Figures. Understanding that these Figures depict only typical embodiments of the invention and are therefore not to be considered limiting of its scope, the invention will be described with additional specificity and detail through the use of the accompanying Figures in which:

FIG. 1A depicts a structural view of the paclitaxel-linked gold nanoparticle, showing multiple paclitaxel molecules covalently linked to a gold nanoparticle through cleavable linkers that contain hydrazone species. In this embodiment, the hydrazone species in the linkers can be degraded in an acidic environment (e.g., pH ~5-6) to release the paclitaxel from the gold nanoparticles. However, under normal physiological conditions (e.g., pH 7-7.4), the hydrazone species remain intact, thereby retaining the paclitaxel molecules on the gold nanoparticles.

FIG. 1B shows the chemical structure of paclitaxel. The 2' site is labeled (paclitaxel becomes substantially inactive if the 2' site is blocked)

FIG. 1C illustrates how a hydrazone species can be degraded in an acidic environment.

FIG. 2A shows the esterification of paclitaxel at the 2' site (the esterification at the 2' site renders the paclitaxel substantially inactive).

FIG. 2B shows the formation of a linker with a hydrazine group at one of its ends.

FIG. 2C shows the coupling of the linker in FIG. 2B to the esterified paclitaxel in FIG. 2A to form a paclitaxel-linker compound, where the paclitaxel becomes coupled to the linker at the 2' site to form a hydrazone species (shown in dotted square).

FIG. 2D shows the coupling of the paclitaxel-linker compound in FIG. 2C to phenol-terminated gold nanoparticles to form the paclitaxel-linked gold nanoparticle shown in FIG. 1A.

DETAILED DESCRIPTION OF EXEMPLARY EMBODIMENTS

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Various methods and therapeutic compositions exist for the delivery of active agents to desired sites in an organism. However, many active agents, such as anti-cancer drugs, act in a non-specific manner against both diseased cells and normal cells. A specific example is paclitaxel, a potent inhibitor of cell proliferation that is widely used in the treatment of various forms of cancer. However, like many other anti-cancer agents and chemotherapeutics, paclitaxel acts non-specifically against both cancer cells and normal cells.

The non-specificity of active agents can cause unnecessary toxicity to healthy cells and tissues. As a result, such non-specificity can lead to undesired side effects in a subject (e.g., nausea, hair loss, reduced immune response, etc.). Such non-specificity can also reduce an active agent's therapeutic efficacy.

To alleviate the above-mentioned problems, active agents have been linked to carriers, such as nanoparticles. However, such methods also suffer from various limitations. For instance, many carriers may not be able to effectively deliver and/or release the active agents at a desired site. Furthermore, the hydrophobic nature of many active agents and nanoparticles may render them insoluble.

Thus, various embodiments of the present disclosure address the above-mentioned problems. Specifically, various embodiments of the present disclosure pertain to therapeutic compositions that comprise: (1) one or more active agents; (2) a cleavable linker; and (3) a nanoparticle that is covalently linked to the active agent(s) through the cleavable linker. In some embodiments, the active agent is substantially inactive when it is covalently linked to the nanoparticle. In further embodiments, the therapeutic compositions of the present disclosure may also be associated with one or more targeting agents. In some embodiments, the cleavable linker is specifically cleaved at a desired treatment site (i.e., tumor site), thereby releasing the active agent at that site.

Figure 1:
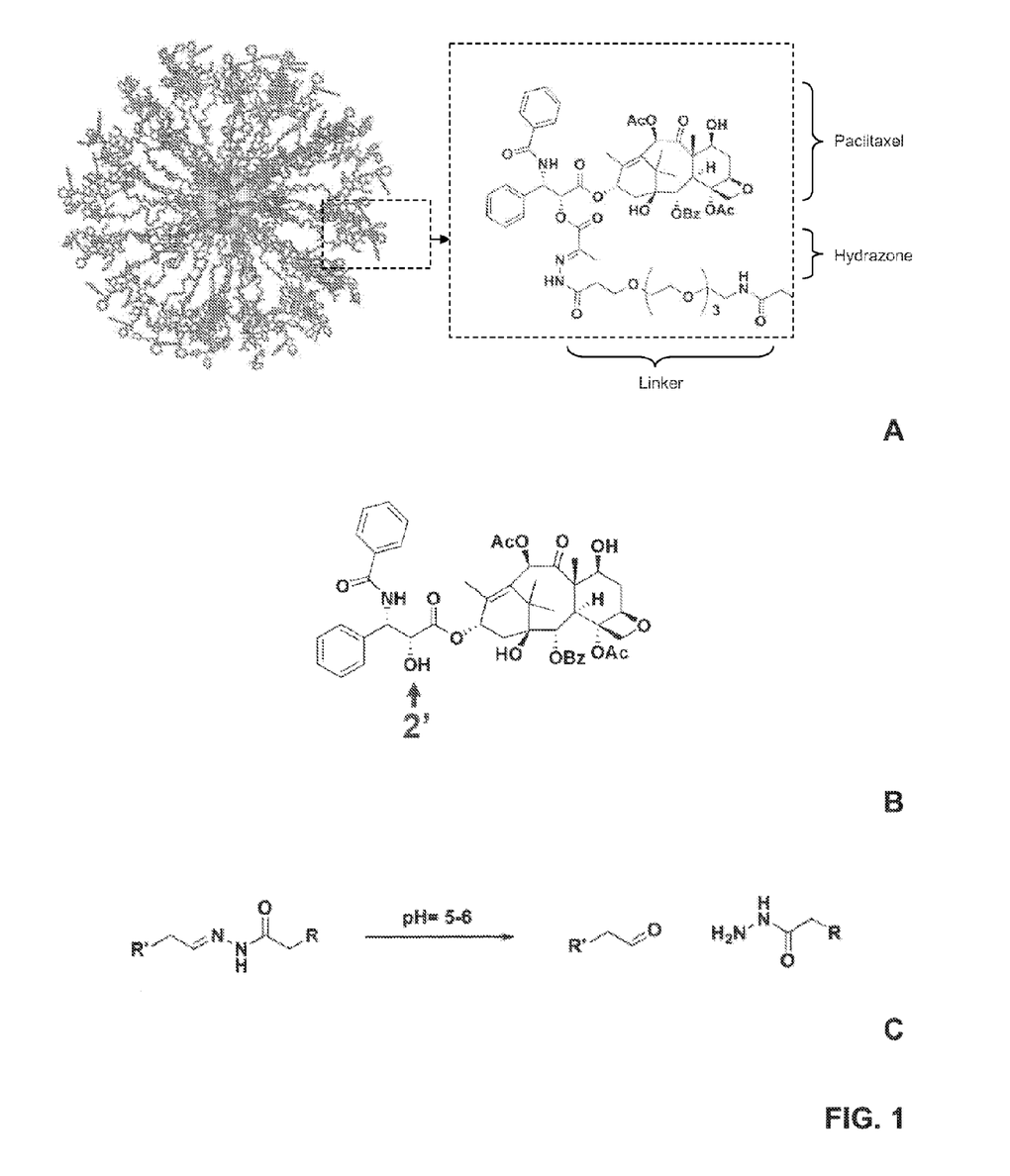
FIG. 1 depicts various aspects of a paclitaxel-linked gold nanoparticle as a specific embodiment of a therapeutic composition.

A specific and non-limiting example of a therapeutic composition in accordance with the present disclosure is shown in FIG. 1A. In this example, the active agent is paclitaxel (shown in FIG. 1B, also known as Taxol® when contained in a commercial excipient, Cremaphor EL), a potent but non-specific inhibitor of cell proliferation that is used in the treatment of various forms of cancer. In this embodiment, the nanoparticle is a gold nanoparticle that is about 2 nm in diameter. As shown in FIG. 1A and discussed in more detail below, multiple paclitaxel molecules are covalently linked to the gold nanoparticle in this example through cleavable linkers that are coupled to the paclitaxel molecules at the 2' site through hydrazone species. As also discussed in more detail below, the blocking of the 2' site renders the paclitaxel molecule substantially inactive.

Without being bound by theory, it is envisioned that under slightly acidic conditions (pH 5-6), which exist at many tumor sites, the hydrazone species of the paclitaxel-linked gold nanoparticles shown in FIG. 1A are degraded (shown in FIG. 1C). This in turn leads to the release of active paclitaxel molecules at or near desired tumor sites. However, under normal physiological conditions (pH 7-7.4), which exist in many normal tissues, the hydrazone species are not cleaved. Therefore, inactive forms of the paclitaxel molecules remain linked to the gold nanoparticles at or near normal tissue sites.

Various aspects of the therapeutic compositions of the present disclosure will now be discussed in more detail.

Active Agents

Active agents of the present disclosure generally refer to biologically active compounds, such as compounds that can be used to treat one or more conditions in a subject (e.g., a human being). For instance, in various embodiments, active agents of the present disclosure may refer to anti-cancer drugs, antibiotics, chemotherapeutics, antioxidants, and/or anti-inflammatory drugs.

The active agents of the present disclosure may also be derived from various compounds. For instance, in various embodiments, the active agents of the present disclosure can be small molecules, proteins, aptamers, DNA, anti-sense oligo nucleotides, miRNA, siRNA, and the like.

In further embodiments, the active agent is an anti-cancer agent, such as paclitaxel, docetaxel, doxorubicin, and the like. In more specific and preferred embodiments, the active agent is paclitaxel.

In further embodiments, the active agent is substantially inactive when it is covalently linked to the nanoparticle. However, the active agent may become active once it is cleaved from the nanoparticle. As used herein, "substantially inactive" refers to a state of an active agent that exhibits a therapeutic activity that is less than the normal or average therapeutic activity of the active agent. The therapeutic activity of an active agent can be determined by the measurement of various parameters, as known by persons of ordinary skill in the art. Such parameters include, without limitation, target binding activities (e.g., as measured by $K_d$ values), inhibition activities (e.g., as measured by $IC_{50}$ values), changes in a dose response curve, changes in survival rates of subjects, and the like. In some embodiments, "substantially inactive" may refer to a state of an active agent that exhibits little or no therapeutic activity.

For instance, paclitaxel is virtually inactive if the 2' site is blocked. Therefore, in some embodiments, paclitaxel may be covalently linked to the nanoparticle through the 2' site. Applicants envision that the inactivation of the active agent in covalently linked form can help prevent any non-specific or undesired effects of the active agent against various non-targeted cells or tissues.

The use of other suitable active agents not disclosed here can also be envisioned by a persons of ordinary skill in the art.

Cleavable Linkers

The cleavable linkers of the present disclosure may have numerous lengths and components. For instance, in some embodiments, the cleavable linkers of the present disclosure may contain one or more polymers, such as polyethylene oxides (PEO), polyesters, polyethylene glycols, polystyrenes, polypropylenes, polyamides, and the like. In further embodiments, the polymers may consist of two or more monomeric units. In more specific embodiments, the polymers may consist of about four to five monomeric units.

Furthermore, the polymers may be homopolymers or heteropolymers. In more specific embodiments, the polymers of the present disclosure may be linked to an active agent at one end and a nanoparticle at another end.

More importantly, the cleavable linkers of the present disclosure contain one or more moieties or sites that can be cleaved and/or degraded under various conditions. The cleavage and/or degradation thereby results in the release of the active agent from the nanoparticle. As set forth below, various cleavable linkers may be used in various embodiments of the present disclosure (e.g., without limitation, chemically cleavable linkers, photo-cleavable linkers, and enzymatically cleavable linkers).

Chemically Cleavable Linkers

In some embodiments, the cleavable linker is a chemically cleavable linker. In such embodiments, one or more moieties and/or sites in the linker may be cleaved and/or degraded by various chemicals and/or reaction conditions (e.g., change in pH). In a more specific embodiment, the cleavable linker is cleaved in an acidic environment (e.g., pH ~5-6).

In more specific and preferred embodiments, the cleavable linker comprises one or more hydrazone species. By way of background, hydrazone species refer to a class of organic compounds with the structure $R_1R_2C=NNH_2$. This structure is illustrated below:

Hydrazone species are usually formed by the reaction of hydrazine with ketones or aldehydes. Furthermore, as illustrated in FIG. 1C, hydrazone species are readily degraded under acidic conditions (i.e., pH ~5-6). Advantageously, many tumor sites have an acidic pH level. Thus, in some embodiments, therapeutic compositions of the present disclosure with cleavable linkers containing hydrazone species may be selectively cleaved at or near tumor sites to selectively release active agents from nanoparticles at those sites.

Various hydrazone species may be used in the cleavable linkers of the therapeutic compositions of the present disclosure. For instance, in some embodiments, $R_1$ and/or $R_2$ may be derived from alkyl, acyl, benzophenone, methyl, ethyl, ester, ether and other similar functional groups. In more specific embodiments, the hydrazone species can include, without limitation, acyl hydrazones, benzophenone hydrazones, acetone hydrazones, N,N-dialkylhydrazones, and the like.

Other chemically cleavable moieties can also be used in the chemical linkers of the present disclosure, as known by persons of ordinary skill in the art.

Photo-Cleavable Linkers

In further embodiments, the cleavable linker is a photo-cleavable linker. In such embodiments, one or more moieties in the linker may be cleaved and/or degraded by photolysis. In various embodiments, the photolysis may be initiated by any photon with sufficient energy to affect the chemical bonds of the linker. Non-limiting examples of such photons include visible light, uv light, x-rays, and gamma rays.

Enzymatically Cleavable Linkers

In further embodiments, the cleavable linker is an enzymatically cleavable linker. In such embodiments, one or more moieties in the linker may be cleaved and/or degraded by various enzymes. For instance, in some embodiments, the enzyme that cleaves and/or degrades the cleavable linker may only be expressed in diseased cells, such as cancer cells.

Nanoparticles

Nanoparticles suitable for use in the present disclosure generally refer to particles that are capable of associating with an active agent, desirably through covalent bonds. Nanoparticles in the present disclosure also refer to particles that are capable of delivering an active agent to a targeted area. In some embodiments, the nanoparticles of the present disclosure are soluble in water.

In some embodiments, the nanoparticles of the present disclosure may be derived from one or more carbon nanotubes (CNTs), including, without limitation, single-walled nanotubes (SWNTs), oxidized SWNTs, multi-walled nanotubes (MWNTs), and oxidized MWNTs. In some embodiments, the nanoparticles of the present disclosure may be derived from graphene, graphene nanoribbons, graphite, graphite oxide nanoribbons, carbon black, oxidized carbon black, and other nanoparticles. In some embodiments, the nanoparticles of the present disclosure may be derived from liposomes.

In more specific and preferred embodiments, nanoparticles of the present disclosure are gold nanoparticles (AuNPs). Without being bound by theory, Applicants envision that the use of gold nanoparticles in the therapeutic compositions of the present disclosure can further exploit the enhanced permeation and retention effect (EPR) associated with tumors.

By way of background, EPR refers to a property where various active agents and macromolecular particles tend to accumulate in tumor tissue more than they accumulate in normal tissue. For instance, in a study, mice bearing tumors and injected with AuNPs retained about eight times more of the AuNPs in the tumors than in the normal cells, which cleared the AuNPs twice as fast as the tumor cells. See Hainfeld et al., *Phys. Med. Biol.* 2004, 49, N309-N315. Thus, Applicants envision that the use of gold nanoparticles in the therapeutic compositions of the present disclosure can provide an additional advantage in enhancing the selectivity and efficacy of active agents in treating cancer (and other similar conditions).

In some embodiments, the nanoparticles of the present disclosure may be functionalized with one or more molecules, polymers, chemical moieties, and/or functional groups. In more specific embodiments, the nanoparticles of the present disclosure may be functionalized with hydroxyl groups and/or polyethylene oxides (PEO). In a more specific embodiment, gold nanoparticles may be functionalized with PEO. In some embodiments, the functionalization occurs on the surfaces of the nanoparticles.

Without being bound by theory, Applicants envision that the functionalization of nanoparticles can improve their solubility. This in turn can improve their availability and efficacy in vivo. In particular, Applicants envision that if nanoparticles are functionalized with one or more molecules, polymers, chemical moieties, and/or functional groups, they should be allowed to circulate for longer periods of time in a living body. As a result, the functionalization would increase the chance of nanoparticles accumulating at or near a desired site (e.g., a tumor site).

The nanoparticles of the present disclosure may also have various sizes. For instance, in some embodiments, the nanoparticles of the present disclosure may be from about 1 nm to about 500 nm in diameter. In other embodiments, the nanoparticles may be from about 1 nm to about 50 nm in diameter. In more specific and preferred embodiments, the nanoparticles of the present disclosure may be about 2 nm in diameter (e.g., ~1.9 nm).

The use of other suitable nanoparticles that have not been not disclosed here can also be envisioned by a person of ordinary skill in the art. As set forth in more detail below, nanoparticles of the present disclosure may also be associated with one or more targeting agents.

Targeting Agents

In some embodiments, therapeutic compositions of the present disclosure may also be associated with one or more targeting agents. For instance, in some embodiments, the targeting agent may be coupled directly to the nanoparticles in the therapeutic composition. In further embodiments, the targeting agent may be coupled to the cleavable linker of the therapeutic composition. In various embodiments, such coupling may occur through covalent and/or non-covalent bonds.

Targeting agents of the present disclosure generally refer to compounds that target a particular cell, organ, and/or tissue for which treatment is desired. In various embodiments, the targeting agent may be compounds such as antibodies, RNA, DNA, aptamers, small molecules, dendrimers, and/or proteins. In more specific embodiments, the targeting agent can be a monoclonal or polyclonal antibody. In particular embodiments, the antibody may be a chimeric antibody or an antibody fragment (e.g., Fab fragment of a monoclonal antibody).

In further embodiments, the targeting agent may be an antibody that specifically targets epidermal growth factor receptors (e.g., Cetuximab). By way of background, epidermal growth factor receptors (EGFRs) are over-expressed in many types of cancer cell lines. Thus, anti-EGFR antibodies and other EGFR inhibitors may be used to deliver anti-cancer agents to cancer cell lines in some embodiments. Other suitable targeting agents can also be envisioned by a person of ordinary skill in the art.

Without being bound by theory, Applicants envision that the use of targeting agents in the therapeutic compositions of the present disclosure can help facilitate their efficacy by directing the active agent to a desired site. However, Applicants note that various therapeutic compositions of the present disclosure may not contain any targeting agents.

Administration of Therapeutic Compositions

Additional aspects of the present disclosure pertain to methods of treating a condition in a subject by administering a therapeutic composition of the present disclosure to the subject. Applicants envision that after the administration of the therapeutic composition, the cleavable linker in the therapeutic composition is cleaved, thereby releasing the active agent from the nanoparticle.

In some embodiments, the cleavable linker in the therapeutic composition may be cleaved in an acidic environment after administration, such as a tumor site. In embodiments where the active agent is substantially inactive when it is covalently linked to the nanoparticle, the cleaving and subsequent release may result in the activation of the active agent.

As set forth in more detail below, the therapeutic compositions of the present disclosure can be used to treat numerous conditions in different subjects through various modes of administration.

Treated Conditions

The methods of the present disclosure can be used to treat various conditions. For instance, in some embodiments, the methods of the present disclosure may be used to treat various types of cancer (e.g., breast cancer, head and neck cancer, colorectal cancer, lymphatic cancer, etc.). In such embodiments, the active agent is an anti-cancer drug (e.g., paclitaxel). Likewise, the targeting agent (if used) may be a compound that recognizes one or more markers on a cancer cell. For instance, the targeting agent may be an antibody that recognizes EGFRs. In more specific embodiments, the cancer-treating methods of the present disclosure may utilize a therapeutic composition where the nanoparticle is a gold nanoparticle, the active agent is paclitaxel, and the cleavable linker contains a hydrazone species (e.g., the therapeutic composition shown in FIG. 1A).

In other embodiments, the methods of the present disclosure can be used to treat microbial infections, such as bacterial, viral, and/or fungal infections. In some of such embodiments, the active agent can be an antibiotic, and the targeting agent (if used) can be an antibody that recognizes one or more markers on the pathogenic microbes and/or infected cells.

In further embodiments, the methods of the present disclosure can be used to treat other conditions, such as inflammation. A person of ordinary skill in the art will also recognize that the methods of the present disclosure can be used to treat other conditions that have not been specifically described above. Furthermore, a person of ordinary skill in the art will recognize that various subjects may be treated by the methods and therapeutic compositions of the present disclosure.

Subjects

In some embodiments, the methods and compositions of the present disclosure may be used to treat human beings. In some embodiments, the subjects being treated may be in need of such treatment for one or more conditions. In other embodiments, the subjects may be non-human animals, such as mice, rats, other rodents, or larger mammals, such as dogs, monkeys, pigs, cattle and horses.

Modes of Administration

The therapeutic compositions of the present disclosure can be administered to subjects by various methods known to persons of ordinary skill in the art. For instance, the therapeutic compositions of the present disclosure can be administered by oral administration, inhalation, subcutaneous administration (sub-q), intravenous administration (I.V.), intraperitoneal administration (I.P.), intramuscular administration (I.M.), and/or intrathecal injection. In further embodiments of the present disclosure, the therapeutic compositions of the present disclosure can be administered by topical application (e.g, transderm, ointments, creams, salves, eye drops, and the like). Additional modes of administration can also be envisioned by persons of ordinary skill in the art.

Formulation of Therapeutic Compositions

Additional embodiments of the present disclosure also pertain to methods of making therapeutic compositions of the present disclosure. Such methods generally comprise covalently linking a nanoparticle to an active agent through a cleavable linker. A person of ordinary skill in the art will recognize that various methods may be used to make the therapeutic compositions of the present disclosure.

Figure 2:
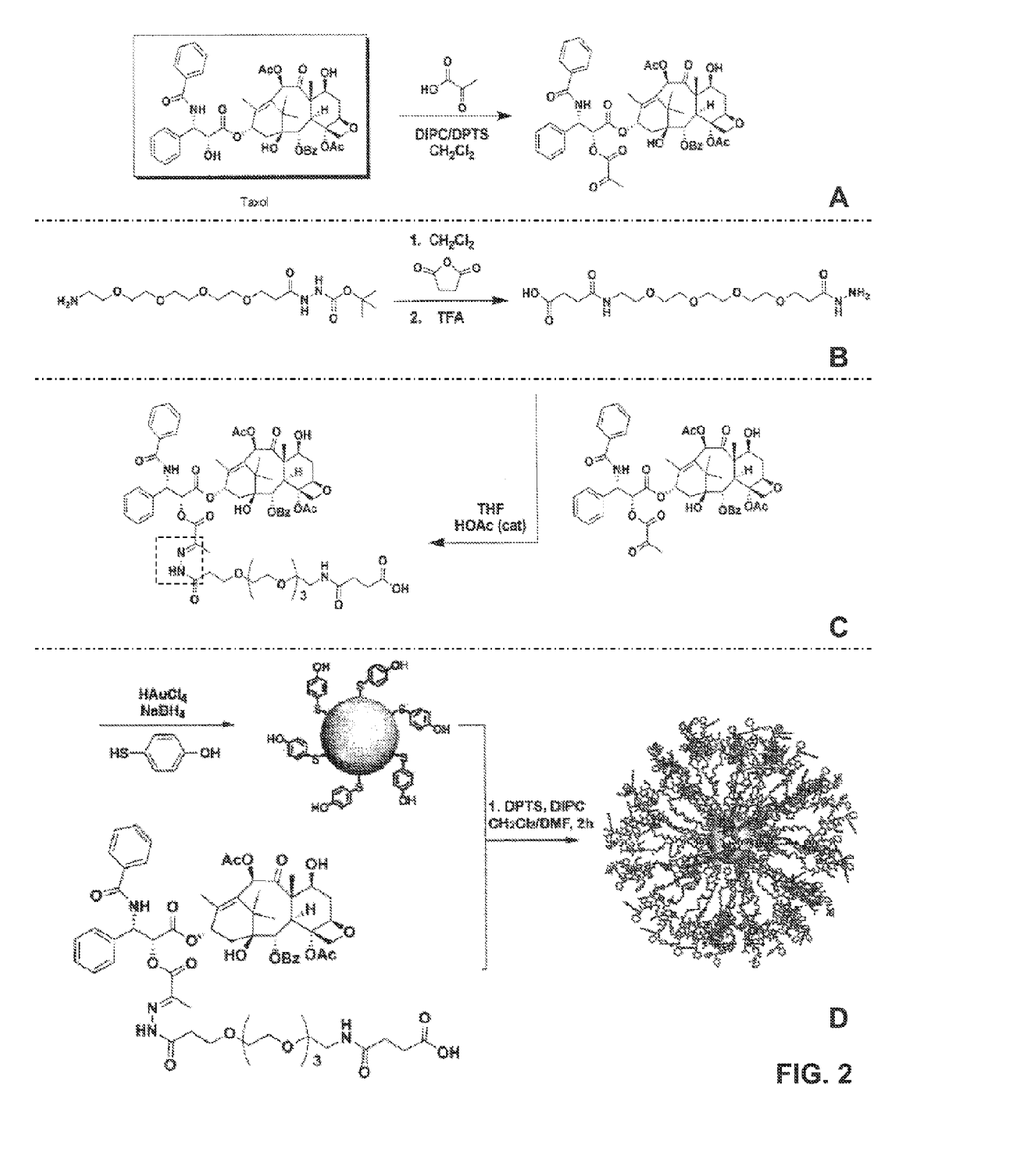
FIG. 2 schematically illustrates how the paclitaxel-linked gold nanoparticle shown in FIG. 1A can be synthesized in some embodiments.

A specific example of a method of making a therapeutic composition is shown in FIG. 2. In this embodiment, paclitaxel is esterified at the 2' site to render it inactive (FIG. 2A). A linker is also formed that contains a hydrazine group at one of its ends (FIG. 2B). Thereafter, the linker is covalently coupled to the esterified paclitaxel to form a paclitaxel-linker compound (FIG. 2C). In this compound, the paclitaxel is coupled to the linker at the 2' site through a hydrazone (shown in dotted square). Next, the paclitaxel-linker compound is coupled to a phenol-terminated gold nanoparticles to form the paclitaxel-linked gold nanoparticle shown in FIG. 1A (FIG. 2D). Various aspects of this embodiment will be discussed in more detail in the Examples below.

Therapeutic compositions of the present disclosure can also be formulated in conventional manners known to persons of ordinary skill in the art. In some embodiments, the formulation may also utilize one or more physiologically acceptable carriers or excipients.

The pharmaceutical compositions can also comprise formulation materials for modifying, maintaining, or preserving various conditions, including pH, osmolarity, viscosity, clarity, color, isotonicity, odor, sterility, stability, rate of dissolution or release, and/or adsorption or penetration of the composition. Suitable formulation materials include, but are not limited to: amino acids (e.g., glycine); antimicrobials; antioxidants (e.g., ascorbic acid); buffers (e.g., Tris-HCl); bulking agents (e.g., mannitol and glycine); chelating agents (e.g., EDTA); complexing agents (e.g., hydroxypropyl-beta-cyclodextrin); and the like.

Additional Embodiments

From the above disclosure, a person of ordinary skill in the art will recognize that the methods and compositions of the present disclosure can have numerous additional embodiments. For instance, in some embodiments, multiple active agents may be covalently linked to a nanoparticle through cleavable linkers. In various embodiments, a therapeutic composition may comprise a plurality of the same active agents. In further embodiments, a therapeutic composition may comprise a plurality of different active agents. In more specific and non-limiting embodiments, therapeutic compositions of the present disclosure may comprise one active agent per nanoparticle, about 2-10 active agents per nanoparticle, or about 50-100 active agents per nanoparticle. In other specific embodiments, the therapeutic compositions of the present disclosure may comprise about 70-75 active agents per nanoparticle. In further embodiments, a therapeutic composition may comprise about 70-75 paclitaxel molecules covalently linked to a single gold nanoparticle.

Reference will now be made to more specific embodiments of the present disclosure and experimental results that provide support for such embodiments. However, Applicants note that the disclosure below is for exemplary purposes only and is not intended to limit the scope of the claimed invention in any way.

EXAMPLES

Additional details about the experimental aspects of the above-described studies are discussed in the subsections below. In general, the Examples below show a method of making a specific therapeutic composition and performing in vitro studies to test its anti-cancer efficacy. See FIGS. 1-3.

Example 1

Synthesis of Paclitaxel-Linked Gold Nanoparticles (PTX-AuNPs)

Initial attempts at hydrazone formation were focused on the reaction of hydrazide terminated linkers with the carbonyl group located at the C-9 position of paclitaxel. These initial attempts were unsuccessful, possibly due to steric hindrance at the C-9 position. Motivated by the need to introduce a more accessible carbonyl into the structure of paclitaxel (PTX), pyruvic acid was chosen, as it can be readily coupled with the C-2' hydroxyl group under standard reaction conditions. Applicants also envisioned that the close proximity of the subsequent hydrazone functionality to the terminal PTX groups would result in the liberation of PTX-2' pyruvate, which should be susceptible to rapid esterase hydrolysis analogous to that demonstrated for both C-2' succinate and dithiodibutyrate systems.

FIG. 2 illustrates the convergent synthetic strategy employed in the manufacturing of the new PTX-AuNP delivery system beginning with the aforementioned conversion of paclitaxel with pyruvic acid under standard DIPC/DPTS conditions (FIG. 2A). In a separate synthesis, commercially available aminotetraethylene glycol t-boc-hydrazide was coupled with glutaric anhydride in order to introduce a terminal carboxyl group that can be coupled to the surface of mercaptophenol-functionalized AuNPs (FIG. 2B). Simply dissolving both agents in an equimolar ratio resulted in quantitative conversion to the desired product in the absence of base or catalyst. Interestingly, the entire carboxyl terminated, free hydrazide linker was produced in a one pot synthesis as TFA (20% final concentration v/v) was subsequently added to the above reaction after one hour to cleave the t-Boc group (FIG. 2B).

Hydrazone formation was then achieved upon the reaction of paclitaxel pyruvate and the hydrazide-terminated linker in the presence of catalytic amounts of TFA with moderate yields (FIG. 2C). TLC analysis of the reaction revealed the near instantaneous formation of a highly UV active product corresponding to the appearance of hydrazone containing intermediate (FIG. 2C). Isolation of the desired product was also simplified as any unreacted hydrazide linker was removed via water extractions and excess PTX-2' pyruvate was removed upon precipitating and rinsing with a 10% solution of EtOAc in hexanes. The synthetic sequence was completed upon the coupling of the carboxyl-terminated compound to the surface of mercaptophenol-coated AuNPs using standard DIPC/DPTS conditions (FIG. 2D). Without being bound by theory, Applicants envision that the relative large size of the final product allows for purification via centrifugation on regenerated cellulose membranes. Prior to structural analysis, the complete removal of excess coupling agents was confirmed by GPC and NMR. The synthetic procedures for the aforementioned steps are described in more detail below.

Synthetic Procedures.

Paclitaxel 2' Pyruvate (FIG. 2A).

To a solution of 100 mg of paclitaxel in 4 mL of $CH_2Cl_2$ were added 60 mg (1.5 equiv) of DPTS and 13 mg (1.3 equiv) of pyruvic acid. Under vigorous stirring, 75 mg (5 equiv) of the coupling agent DIPC were added to catalyze ester formation. Upon addition of DIPC, the colorless solution immediately became yellow in color and progressed to a dark orange color as the reaction continued. Near complete consumption of starting PTX was observed after 2-3 hours, as evidenced by TLC. The reaction was quenched upon removal of DPTS via three water extractions. The mixture was then dried over $Na_2SO_4$ and solvent reduced under vacuum while DIPC was subsequently removed by precipitating the crude product from hexanes. The product was then further isolated by column chromatography eluting with a 4:1 mixture (v/v) of EtOAc:hexanes providing 98 mg (91% yield) of a white powder. $R_f$=0.60. $^1$H NMR (CDCl$_3$) δ 1.14 (s, 3H), 1.25 (s, 3H), 1.69 (s, 3H), 1.80-1.96 (broad, 4H), 2.05 (s, 3H), 2.23 (s, 3H), 2.45 (m, 1H), 3.83 (d, 1H), 4.10 (m, 1H), 4.21 (d, 1H), 4.32 (d, 1H), 4.45 (m, 1H), 5.00 (d, 1H), 5.50 (d, 1H), 5.69 (d, 1H), 6.05 (d, 1H), 6.20-6.30 (m, 2H), 7.04 (d, 1H), 7.33-7.48 (m, 10H), 7.63 (m, 1H), 7.74 (d, 2H), 8.16 (d, 2H).

Hydrazidotetraethylene Glycol Amide Glutarate (FIG. 2B).

15 mg of glutaric anhydride were first placed in an 8 mL glass vial and dissolved in a minimal amount of THF prior to dilution with 1.5 mL of CH$_2$Cl$_2$ (a few drops of THF are required as the anhydride has limited solubility in methylene chloride). Amide formation was immediate upon the dropwise addition of a solution containing 50 mg (1.0 equiv) of commercially available aminotetraethylene glycol t-boc hydrazide in 0.50 mL of CH$_2$Cl$_2$. Upon GPC analysis, the reaction was determined to be complete after one hour due to the existence of only one product peak. Solvent was then removed under vacuum and prepared for structural analysis. $^1$H NMR (CDCl$_3$) δ 1.44 (s, 9H)$^a$, 1.96 (m, 2H), 2.30-2.43 (broad, 4H), 2.54 (m, 2H), 3.40 (m, 2H), 3.63 (m, 12H), 3.72 (m, 4H), 7.60 (s, 1H), 8.94 (s, 1H). $^a$t-boc protons.

Paclitaxel-Hydrazone Linker Compound (PTX-L-COOH) (FIG. 2C).

Prior to hydrazone formation, the t-Boc protected hydrazide linker was first treated with a solution of 20% TFA in CH$_2$Cl$_2$. After 30 minutes, TFA and residual solvent were removed under vacuum pressure and the resulting colorless oil was dissolved in 1.5 mL of THF. Following the liberation of the t-Boc group, 50 mg of paclitaxel pyruvate was dissolved in 1 mL of THF and added to the hydrazide linker solution. Hydrazone formation was then catalyzed by the addition of 1-2 drops of TFA. Progress of the reaction was monitored via TLC (4:1 EtOAc:hexanes) based on the decrease in UV intensity of compound paclitaxel pyruvate ($R_f$=0.60), and the appearance of a highly UV active spot with an $R_f$ value of 0. Upon completion, TFA and solvent were removed under high vacuum, and the residual product was precipitated from hexanes. Excess reactant products were then removed by washing the precipitate with a 10% solution of EtOAc in hexanes until it was no longer detectable in TLC (3-4 washes). Typical yields for this reaction are moderate (approximately 70% based on the starting linker). $R_f$=0. $^1$H NMR (CDCl$_3$) δ 1.14 (s, 3H), 1.25 (s, 3H), 1.69 (s, 3H), 1.80-1.96 (broad, 6H), 2.05 (s, 3H), 2.23 (s, 3H), 2.30-2.40 (broad, 4H) 2.45 (m, 1H), 2.55 (m, 2H), 3.45 (m, 2H), 3.65 (m, 12H), 3.83 (m, 5H), 4.20 (m, 1H), 4.30 (d, 1H), 4.45 (m, 1H), 4.98 (d, 1H), 5.50-5.70 (m, 2H), 6.00 (d, 1H), 6.20-6.30 (m, 2H), 7.25-7.55 (m, 11H), 7.60 (m, 1H), 7.74 (d, 2H), 8.16 (d, 2H).

Formation of PTX-AuNPs.

Preactivation of the carboxyl terminated intermediate was achieved upon the addition of 20 mg of DIPC to a 3 mL solution of methylene chloride containing 15 mg of Paclitaxel-hydrazone linker compound (PTX-L-COOH) and 25 mg of DPTS. Immediately following the addition of DIPC, a solution of 5 mg of mercaptophenol-functionalized AuNPs in 0.30 mL of DMF was added to the above mixture. The reaction was monitored by GPC and additional amounts of PTX-L-COOH were added in 3-5 mg aliquots until saturation of nanoparticle was complete based on the sharpness and quality of the product signal in GPC. After 3-4 hours, the reaction was quenched upon DPTS removal via three extractions with DI water followed by drying of the crude solution over Na$_2$SO$_4$. Methylene chloride was removed under vacuum, and the residual product was then diluted in DMF and placed on regenerated cellulose membrane filters (Millipore MWCO 30 kDa) and subjected to 3 rounds of centrifugation at 40 minutes each before being analyzed for purity by GPC. Following complete removal of all low molecular weight impurities, the formed AuNP(PTX)$_n$ was diluted with CH$_2$Cl$_2$ and DMF was removed via water extractions. The product solution was again dried over Na$_2$SO$_4$ and the final product precipitated from hexanes and dried under high vacuum leaving 14 mg of a light brown powder. $^1$H NMR (CDCl$_3$) δ 1.14 (s, 3H), 1.25 (s, 3H), 1.69 (s, 3H), 1.80-1.96 (broad, 6H), 2.05 (s, 3H), 2.23 (s, 3H), 2.30-2.40 (broad, 4H) 2.45 (m, 1H), 2.55 (m, 2H), 3.45 (m, 2H), 3.65 (m, 12H), 3.83 (m, 5H), 4.20 (m, 1H), 4.30 (d, 1H), 4.45 (m, 1H), 4.98 (d, 1H), 5.50-5.70 (m, 2H), 6.00 (d, 1H), 6.20-6.30 (m, 2H), 7.25-7.55 (m, 11H), 7.60 (m, 1H), 7.74 (d, 2H), 8.16 (d, 2H).

Example 2

In Vitro Efficacy of PTX-AuNPs

Figure 3:
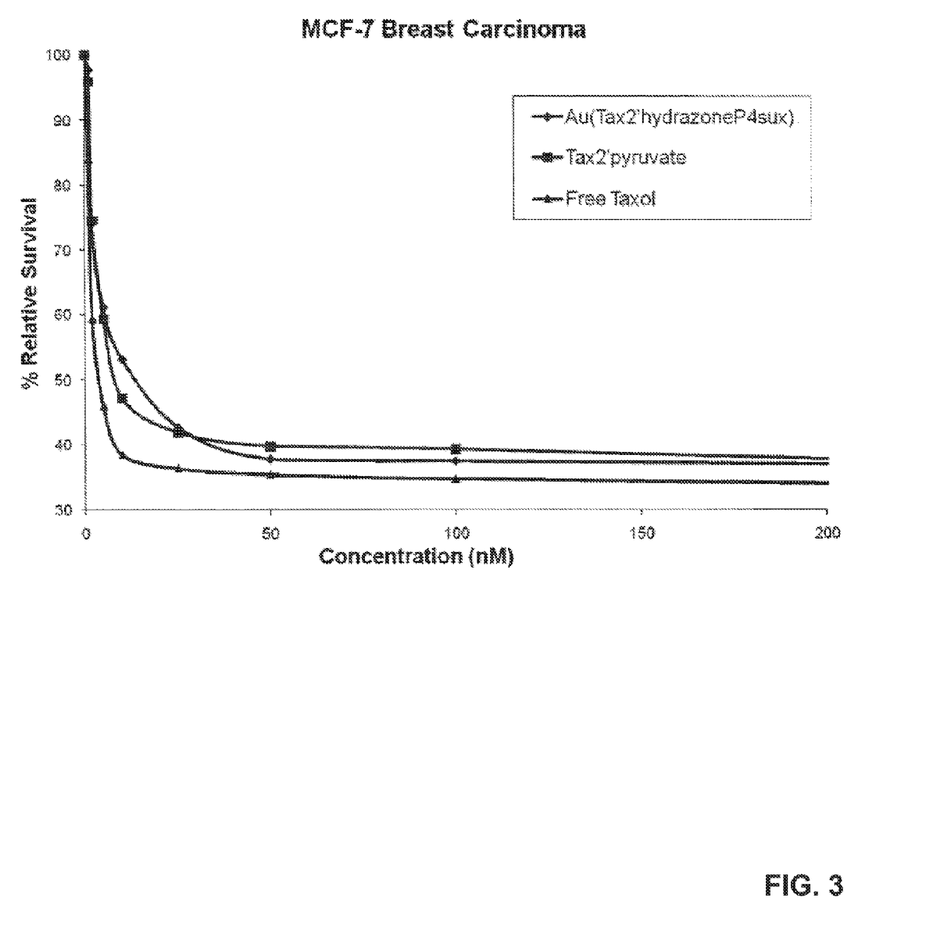
FIG. 3 shows experimental results obtained from in vitro studies that tested the in vitro efficacy of the paclitaxel-linked gold nanoparticles (labeled as "Au(Tax2' hydrazoneP4sux)") in MCF-7 breast carcinoma cells.

The antiproliferative capabilities of PTX-AuNPs from Example 1 were first investigated in vitro. To this end, cellular assays were performed to compare the ability of the PTX-AuNPs to inhibit cell growth relative to the parent drug. Briefly, MCF-7 breast cancer cells were treated over a range of concentrations (based on equivalent PTX content) for all samples and relative cell survival was measured 72 hours post treatment following the MTT protocol. Additionally, the paclitaxel pyruvate compound was also analyzed, as it represented the agent released from the gold surface upon degradation of the hydrazone linker. Results of these experiments are shown in FIG. 3.

MCF-7 cells were plated in 6 well plates and allowed to proliferate until approximately 80-90% confluent. Once optimal confluency was reached, increasing concentrations of PTX-AuNPs were added to each well in order to ensure sufficient uptake for imaging (up to 100 µg/mL). Following 12 hours of incubation with PTX-AuNPs, the cells were fixed with a solution of gluteraldehyde and imaged by transmission electron microscopy (TEM). MCF-7 breast cancer cells were plated in 96-well plates at a concentration of 4,000 cells/well (100 µL/well) and allowed to attach for 24 hours. After successful attachment, 100 µL of media containing the compounds of interest and free paclitaxel (1, 2, 5, 10, 25, 50, 100 and 500 nM with respect to paclitaxel) were added to each well, with each sample concentration having 5 replicates. 72 hours post treatment, 25 µL of yellow MTT solution (5 mg/mL in PBS) were added to each well and incubated at 37° C. for 3-4 hours to allow for sufficient conversion to the blue formazan precipitate. Next, the media was removed followed by the addition of 100 µL of DMSO to dissolve the blue formazan metabolite. Upon agitating the plates for 2 minutes, absorbance values were recorded using a plate reader (Gene Mate, BioTek) equipped with a 570 nm filter.

As well-known, commercially available paclitaxel exhibits high potency towards inhibiting cell growth, as evidenced by an IC$_{50}$ value of approximately 4 nM. Interestingly, paclitaxel pyruvate displays a virtual retention of toxicity (IC$_{50}$=9 nM), providing additional evidence of the high susceptibility of PTX-2' esters to enzymatic hydrolysis. This potent inhibitory quality of paclitaxel pyruvate confirms the usefulness of a hydrazone strategy towards effecting intracellular drug delivery based on a AuNP carrier.

Another result obtained from this study is the demonstrated ability of final gold nanoparticles product to inhibit cell growth, affecting 50% inhibition at a concentration of approximately 12 nM. Furthermore, and without being bound by theory, the difference in IC$_{50}$ values for paclitaxel pyruvate and PTX-AuNPs (3 nM) suggests that hydrolysis of the hydrazone linker is indeed rapid upon cellular internalization. Additionally, the 8 nM increase in the IC$_{50}$ value for PTX-AuNPs compared to that of free paclitaxel suggests the near quantitative delivery of surface bound drug. In addition, the increased activity observed for the final product also suggests that once cleaved, free paclitaxel does not remain confined in the endosome. It is hypothesized that the released drug is capable of passive diffusion through the endosomal membrane in a manner analogous to that of commercially available paclitaxel diffusing through the external cell membrane.

In brief, Applicants envision that the administration of the above-mentioned paclitaxel-linked gold nanoparticles will provide various advantages when used in vivo. Such advantages include, without limitation: (1) passive accumulation of the paclitaxel-linked gold nanoparticles near tumor sites due to the previously-described EPR effect; (2) faster clearance of paclitaxel from normal tissues; (3) the site specific release of paclitaxel from the gold nanoparticles at tumor sites; and (4) the retainment of paclitaxel on gold nanoparticles in an inactive form near normal tissues.

Without further elaboration, it is believed that one skilled in the art can, using the description herein, utilize the present invention to its fullest extent. The embodiments described herein are to be construed as illustrative and not as constraining the remainder of the disclosure in any way whatsoever. While some embodiments may involve particular mammals, the present invention encompasses other mammals, including experimental animals, companion animals, farm animals, primates and humans. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A therapeutic composition comprising:
   paclitaxel; and
   a nanoparticle, wherein the nanoparticle is selected from the group consisting of carbon nanotubes, gold nanoparticles, liposomes, graphenes, graphites, and derivatives thereof, wherein the paclitaxel is covalently linked through the 2' site of paclitaxel to the nanoparticle through a cleavable linker by formation of paclitaxel 2' pyruvate, wherein the paclitaxel 2' pyruvate is esterified and wherein the cleavable linker comprises a hydrazone species.

2. The therapeutic composition of claim 1, wherein the paclitaxel is substantially inactive when it is covalently linked to the nanoparticle.

3. The therapeutic composition of claim 1, wherein the cleavable linker is a chemically cleavable linker.

4. The therapeutic composition of claim 1, wherein the hydrazone species is selected from the group consisting of acyl hydrazones, benzophenone hydrazones, acetone hydrazones, and N,N-dialkylhydrazones.

5. The therapeutic composition of claim 1, wherein the cleavable linker is cleaved in an acidic environment, and wherein the cleavage results in the release of the paclitaxel from the nanoparticle.

6. The therapeutic composition of claim 1, wherein the nanoparticle is a gold nanoparticle.

7. The therapeutic composition of claim 1, wherein the nanoparticle has a diameter of about 2 nm.

8. The therapeutic composition of claim 1, wherein the nanoparticle is functionalized with one or more functional groups and/or polymers.

9. The therapeutic composition of claim 1, wherein the nanoparticle is functionalized with polyethylene oxide.

10. The therapeutic composition of claim 1, further comprising a targeting agent.

11. The therapeutic composition of claim 10, wherein the targeting agent is selected from the group consisting of antibodies, proteins, RNA, DNA, aptamers, small molecules, and dendrimers.

12. The therapeutic composition of claim 1, further comprising a plurality of active agents covalently linked to the nanoparticle through one or more cleavable linkers.

* * * * *